United States Patent [19]

Lersmacher et al.

[11] Patent Number: 4,476,163

[45] Date of Patent: Oct. 9, 1984

[54] METHOD OF MAKING CRUCIBLES FOR FLAMELESS ATOMIC ABSORPTION SPECTROSCOPY

[75] Inventors: Bernhard Lersmacher, Aachen, Fed. Rep. of Germany; Ludovicus W. J. van Kollenburg, Veldhoven, Netherlands

[73] Assignee: U.S. Philips Corporation, New York, N.Y.

[21] Appl. No.: 213,431

[22] Filed: Dec. 5, 1980

[30] Foreign Application Priority Data

Dec. 8, 1979 [DE] Fed. Rep. of Germany ....... 2949476

[51] Int. Cl.$^3$ ...................... C23C 11/00; C23C 13/00
[52] U.S. Cl. .................................. 427/249; 427/255.5
[58] Field of Search ............ 427/248.1, 249, DIG. 11, 427/255.4, 402, 376.1, 255.5, 255.7, 255.6

[56] References Cited

U.S. PATENT DOCUMENTS

| | | | |
|---|---|---|---|
| 3,138,435 | 6/1964 | Diefendorf | 427/249 |
| 3,369,920 | 2/1968 | Bourdeau et al. | 427/249 |
| 3,549,847 | 12/1970 | Clark et al. | 427/249 |
| 3,619,286 | 11/1971 | Gutnajer | 427/DIG. 11 |
| 3,715,253 | 2/1973 | Olcott | 427/249 |
| 3,720,499 | 3/1973 | Hirayama et al. | 427/249 |
| 3,811,927 | 5/1974 | Joo et al. | 427/248.1 |
| 3,944,686 | 3/1976 | Froberg | 427/249 |

*Primary Examiner*—Sadie L. Childs
*Attorney, Agent, or Firm*—Paul R. Miller

[57] ABSTRACT

A method of making crucibles for flameless atomic spectroscopy comprises coating carbon crucible preforms with pyrolytic graphite in a reaction vessel by deposition of the graphite from a gas phase wherein the carbon crucible preforms are removed from the reaction vessel after cooling to room temperature and are re-introduced into the reaction vessel orientated in different positions before application of a second or subsequent coating to give a total thickness of the coatings of 20 to 80 $\mu$m.

10 Claims, No Drawings

METHOD OF MAKING CRUCIBLES FOR FLAMELESS ATOMIC ABSORPTION SPECTROSCOPY

SUMMARY

The useful life of crucibles coated with pyrolytic graphite by deposition from the gas phase is increased to more than 3,000 injections if the coated base is rearranged after cooling from deposition temperature to room temperature and then coated at least once more with pyrolytic graphite, to give layers of pyrolytic graphite to a total thickness of 20 to 80 μm.

The invention relates to a method of making crucibles for flameless atomic absorption spectroscopy (AAS) where each carbon preform is coated with pyrolytic graphite in a reaction vessel by reactive deposition from the gas phase (CVD process).

AAS crucibles are known for use as containers and heating devices for the analysis of samples. Tubular bodies in particular are known for use as crucibles from German patent specifications Nos. 20 06 032 and 21 48 777. The crucibles generally consist of a high-temperature-resistant, electrically conductive material, since each sample to be analysed is usually heated by electrical resistance heating of the crucibles which are connected to an electric current. Other methods of heating, e.g. inductive or radiation heating, can, of course, also be used.

The preferred material for such crucibles is carbon, especially in the form of pure-spectrum electrical graphite. The prior art also teaches the use of crucibles of vitreous carbon (published German patent application No. 20 34 960).

One disadvantage of the aforementioned graphite is its porosity which results in that the substance to be analysed penetrates into the crucible walls, so that, if the crucible is used repeatedly, residues of substance from one analysis can falsify the results of subsequent analyses. This phenomenon is known as the "memory effect". In addition, penetration of analysed substances into the crucible walls adversely affects the otherwise obtainable limits of detection and sensitivity of the analysis. In particular, penetration greatly shortens the useful life of the crucibles as it can also have a highly corrosive action during the analysis when temperatures of up to 3000° C. may occur.

To reduce or completely eliminate the above disadvantages, we have found that access to the pore channels (and specially to corrosion-prone grain boundaries) of the graphite should be sealed off. This may be done, for instance, by applying a thin coating of pyrolytic graphite, which provides an effective diffusion proof barrier even at thicknesses of a few microns (5 to 10 μm). The result of this procedure is markedly to increase sensitivity, or mean absorbance, and also, especially, the useful life, according to our own measurements. The state of the art may be summarised by saying that uncoated graphite crucibles will withstand 10 to 100 analysis (German patent application No. 20 34 960 quotes a figure of 200), while those coated with pyrolytic graphite are re-usable even more often and at the same time the sensitivity is improved. The data in the literature on the proportionate increase in the useful life are, however, in part, contradictory and unreliable. Reference may be made in this connection to the prior publication by Manning and Edinger in Atomic Absorption Newsletter, vol. 15, No. 2, March-April 1976, pp. 42–44. The subject here is "in situ" coating. The information given shows that increased sensitivity is indeed achieved, but the re-usability rate of about 100-fold represents no special advance as against uncoated crucibles. Moreover, in situ coating is very troublesome, difficult to monitor for coating quality and apparently has to be repeated relatively often, e.g. at the most after eight analyses.

One object of the invention is to provide a highly sensitive crucible with the primary advantage lying in a markedly lengthened useful life. The technical significance of long useful lives becomes particularly clear when applied to automated AAS equipment, as used, for instance, in the routine monitoring of impurities in water or the atmosphere.

This object is achieved by the invention by means of a method of the type described in the preamble, where the croated preforms are removed from the reaction vessel after cooling from deposition temperature to room temperature, and they are replaced in the reaction vessel so that the individual coated preforms assume different positions in comparison with their positions in the previous coating process and they are then coated with pyrolytic graphite at least once more to give a total pyrolytic graphite coating thickness of 20 to 80 μm.

The preferred thicknesses for the coatings amounts to a total of 20 to 40 μm, in particular 30 to 40 μm.

Coating thicknesses of more than 80 μm are not advisable because of the risk of flaking. Moreover, the electrical resistance of a crucible changes very considerably as the coating thickness increases, and this has often been found to be a drawback in the operation of the analysis apparatus used.

The preforms are removed after cooling and reinserted so as to take up different positions every time, in the manner described, when more than two coating processes are required.

The preforms may be inserted and reinserted by filling a basket-like graphite container in the reaction vessel.

In the process of the reactive deposition of pyrolytic graphite, the deposition temperature is about 2000° C.

It is advisable to undertake at least one of the successive coating process by means of hot-wall pyrolysis, as described in Philips Technical Review, vol. 37 (1977), No. 7, pp. 161 to 168.

The use of this method has the advantage that a number of crucibles may be coated simultaneously, which has important economic significance. The process is unaffected by the shape and position of the individual crucibles, since heating to uniform temperatures and thus the uniformity of the deposited coatings inside the crucibles are ensured. The individual crucibles need not be arranged individually in the reactor vessel, but are simply shovelled in. This may give rise to a certain drawback of the method, since there will of necessity be points of contact between the crucibles introduced into the coating area which may result in uneven thicknesses in the outer coating. This drawback is largely compensated by the fact that the heap is rearranged, i.e. in subsequent coating processes, each individual crucible will normally assume a different position in the reactor and hence have different points of contact with its neighbours. This rearrangement or redistribution may be performed several times after every precoating process, but it has been found that a single rearrangement, and hence a two-stage coating process, is often sufficient.

In one embodiment the preforms to be coated are introduced into the reaction vessel comprising a pyrolysis apparatus in a random arrangement and after reintroduction into the reaction vessel are shifted about at room temperature before the further coating processes are performed.

The preforms to be coated generally consist of graphite, and especially electrical graphite. It is often advantageous to coat preforms of vitreous carbon. It is of special advantage to use the method of the invention to coat preforms made of rigid carbonised fabric based on curable synthetic resins convertible into vitreous carbon, e.g. phenol or cresol resin, and cotton fabric. Such crucible preforms are proposed in German patent application No. P 27 02 189.2.

In a further embodiment of the method of the invention, the surfaces of the preforms, especially the inner surfaces of the crucibles coming into direct contact with the sample to be analysed at the start of analysis, are as highly polished as possible before coating.

The method of the invention produces crucibles noteworthy in particular for high uniformity and a good structure of the protective coatings of pyrolytic graphite both inside and outside. It was remarkable to find in the course of a large number of measurements that the crucibles made by the method of the invention exhibit extremely long useful lives (that is, in having a very large number of injections, analysis etc.) if the pyrolytic graphite coatings were more than 20 $\mu$m thick, and especially between 30 and 40 $\mu$m thick.

EXAMPLE 1

600 tubular graphite preforms 28 mm long, 8 mm in outside diameter and 6 mm in inside diameter were all introduced at the same time into a hot-wall reaction vessel and given a coating of oriented pyrolytic graphite in six coating cycles each one hour long, thus with five redistribution processes undertaken after cooling to room temperature by their removal from the reaction vessel and reinsertion in different positions for the individual preforms, with a repetition of all the individual steps needed for coating with pyrolytic graphite, i.e. the evacuation of the reaction vessel by means of pumping to a final pressure of $1.33 \times 10^{-6}$ bar or lower, heating the reaction vessel to about 2000° C. and the introduction of a metered quantity (2 mol/h here) of the gas to by pyrolysed (propane in this case).

The final total coating thickness was about 37 $\mu$m.

A coated crucible according to Example 1 was found to withstand 610 to 1200 cycles in a test performed in actual conditions in which an analysis solution of aluminium in 0.1 N.nitric acid was injected and the prescribed temperature-time cycle (up to T=3000 K) was implemented.

EXAMPLE 2

Crucibles made in the same way withstood 320 to 700 injections with the same temperature-time cycles when a solution of aluminium in 0.1 N.perchloric acid was injected instead of 0.1 N.HNO$_3$.

EXAMPLE 3

250 graphite preforms were coated with oriented pyrolytic graphite under otherwise identical conditions. Coating to a total thickness of about 40 $\mu$m was performed in two steps, i.e. with only one rearrangement.

In the analysis conditions set out in Examples 1 and 2, useful lives of more than 300 injections were attained. At this stage, the tests were stopped, although the crucibles were still perfectly usable.

What is claimed is:

1. A method for making crucibles for flameless atomic absorption spectroscopy comprising the steps of coating preforms of carbon with pyrolytic graphite in a reaction vessel by reactive deposition from gas phase, removing coated preforms from said reaction vessel after cooling from deposition temperature to room temperature, reintroducing said coated preforms into said reaction vessel so that individual coated preforms assume a different position, recoating said coated preforms with pyrolytic graphite in at least one additional step, and repeating said steps of removing, reintroducing and recoating until pyrolytic graphite coatings are produced on said preforms to a total thickness of 20 to 80 $\mu$m.

2. A method according to claim 1, wherein said coatings are produced to a total thickness of 30 to 40 $\mu$m.

3. A method according to claims 1 or 2, wherein at least one of said coatings and recoatings is produced by hot-wall pyrolysis.

4. A method according to claim 3, wherein said preforms are introduced into said reaction vessel in a random arrangement, and after said step of reintroducing, said coated preforms are moved about at room temperature before said step of recoating is carried out.

5. A method according to claim 4, wherein said preforms are made of carbonized rigid fabric based on curable synthetic resins convertible into vitreous carbon and cotton fabric.

6. A method according to claim 5, wherein said preforms have surfaces which are highly polished before coating.

7. A method according to claims 1 or 2, wherein said preforms are graphite.

8. A method according to claims 1 or 2, wherein said preforms are vitreous carbon.

9. A method according to claims 1 or 2, wherein said preforms are introduced into said reaction vessel in a random arrangement, and after said step of reintroducing, said coated preforms are moved about at room temperature before said step of recoating is carried out.

10. A method according to claims 1 or 2, wherein said preforms are made of carbonized rigid fabric based on curable synthetic resins convertible into vitreous carbon and cotton fabric.

* * * * *